United States Patent
Taguchi et al.

(10) Patent No.: US 10,258,813 B2
(45) Date of Patent: Apr. 16, 2019

(54) MEDICAL IMAGE PROCESSING APPARATUS, TREATMENT SYSTEM, MEDICAL IMAGE PROCESSING METHOD, AND MEDICAL IMAGE PROCESSING PROGRAM

(71) Applicant: Kabushiki Kaisha Toshiba, Minato-ku (JP)

(72) Inventors: Yasunori Taguchi, Kawasaki (JP); Ryusuke Hirai, Shinagawa (JP); Yukinobu Sakata, Kawasaki (JP); Kyoka Sugiura, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/914,091

(22) Filed: Mar. 7, 2018

(65) Prior Publication Data

US 2018/0193670 A1 Jul. 12, 2018

Related U.S. Application Data

(63) Continuation of application No. 14/847,791, filed on Sep. 8, 2015, now Pat. No. 10,016,625.

(30) Foreign Application Priority Data

Dec. 19, 2014 (JP) ................... 2014-257910

(51) Int. Cl.
*A61N 5/10* (2006.01)
*G06T 7/246* (2017.01)
(Continued)

(52) U.S. Cl.
CPC ......... *A61N 5/1049* (2013.01); *G06K 9/3241* (2013.01); *G06K 9/6211* (2013.01);
(Continued)

(58) Field of Classification Search
CPC combination set(s) only.
See application file for complete search history.

(56) References Cited

U.S. PATENT DOCUMENTS 7,570,738 B2 * 8/2009 Khamene ............... A61B 6/032
378/20
8,467,497 B2 * 6/2013 Lu ........................ A61N 5/1049
378/65

(Continued)

FOREIGN PATENT DOCUMENTS

JP     2006-51199 A    2/2006
JP     4064952 B2      3/2008
(Continued)

OTHER PUBLICATIONS

Ying Cui, et al., "Multiple template-based fluoroscopic tracking of lung tumor mass without implanted fiducial markers" Physics in Medicine and Biology, vol. 52, No. 20, 2007, pp. 6229-6242.

*Primary Examiner* — Tsung Yin Tsai
(74) *Attorney, Agent, or Firm* — Oblon, McClelland, Maier & Neustadt, L.L.P.

(57) ABSTRACT

A medical image processing apparatus of an embodiment has acquisitor, a first landmark detector, and an estimator. The acquisitor acquires a perspective image of an object to be treated imaged by an imaging apparatus. The first landmark detector detects a position of a landmark that appears in the perspective image acquired by the acquisitor. The estimator, based on relationship information indicating a relationship between the position of landmark and the position of a target, estimates the position of the search-for location of the object to be treated from the position of the landmark detected by the first landmark detector.

22 Claims, 17 Drawing Sheets

(51) Int. Cl.
    *G06K 9/32*     (2006.01)
    *G06K 9/62*     (2006.01)
(52) U.S. Cl.
    CPC ...... *G06T 7/246* (2017.01); *A61N 2005/1051*
        (2013.01); *A61N 2005/1061* (2013.01); *G06K*
            *2209/05* (2013.01); *G06T 2207/10081*
        (2013.01); *G06T 2207/10124* (2013.01); *G06T*
            *2207/20081* (2013.01); *G06T 2207/20104*
        (2013.01); *G06T 2207/30048* (2013.01); *G06T*
                                *2207/30061* (2013.01)

(56)            References Cited

U.S. PATENT DOCUMENTS

| | | | |
|---|---|---|---|
| 8,509,383 | B2 | 8/2013 | Lu et al. |
| 8,679,012 | B1* | 3/2014 | Kayyali ............... A61B 5/0002 600/301 |
| 8,751,200 | B2 | 6/2014 | Takai et al. |
| 9,368,499 | B2* | 6/2016 | Hong ................. H01L 27/1203 |
| 2009/0116616 | A1* | 5/2009 | Lu ........................ A61N 5/1049 378/65 |
| 2010/0249593 | A1* | 9/2010 | Takeguchi ............... A61B 8/00 600/443 |
| 2011/0044429 | A1 | 2/2011 | Takahashi et al. |
| 2012/0226152 | A1 | 9/2012 | Porikli |
| 2013/0018232 | A1 | 1/2013 | D'Souza et al. |
| 2013/0223702 | A1* | 8/2013 | Holsing ................. A61B 5/113 382/128 |
| 2015/0018595 | A1 | 1/2015 | Taguchi et al. |
| 2015/0094516 | A1 | 4/2015 | Taguchi et al. |
| 2016/0136458 | A1 | 5/2016 | Taguchi et al. |

FOREIGN PATENT DOCUMENTS

| | | |
|---|---|---|
| JP | 2008-154861 A | 7/2008 |
| JP | WO 2009/072618 A1 | 6/2009 |
| JP | 2011-502010 A | 1/2011 |
| JP | 2012-506734 A | 3/2012 |
| JP | 5604306 B2 | 10/2014 |
| JP | 2014-212820 A | 11/2014 |
| JP | 2015-16161 A | 1/2015 |
| JP | 2015-66275 A | 4/2015 |
| JP | 2016-96902 A | 5/2016 |
| WO | WO 2010/058863 A1 | 5/2010 |

\* cited by examiner

MEDICAL IMAGE PROCESSING APPARATUS, TREATMENT SYSTEM, MEDICAL IMAGE PROCESSING METHOD, AND MEDICAL IMAGE PROCESSING PROGRAM

CROSS-REFERENCE TO RELATED APPLICATION

This application is a continuation of and claims the benefit of priority under 35 U.S.C. § 120 from U.S. application Ser. No. 14/847,791 filed Sep. 8, 2015, and claims the benefit of priority under 35 U.S.C. § 119 from Japanese Patent Application No. 2014-257910 filed Dec. 19, 2014; the entire contents of each of which are incorporated herein by reference.

FIELD

Embodiments described herein relate to a medical image processing apparatus, a treatment system, a medical image processing method, and a medical image processing program.

BACKGROUND

In radiotherapy, a CT (computed tomography) image in the affected area is first imaged beforehand at the planning stage, and a treatment plan is established. At the treatment stage, the affected area is treated by an affected area being radiated by a treatment beam. The affected area might move because of respiration or heartbeat, intestinal movement, or the like. Known treatment methods of handling this are the gated irradiation method and the tracking irradiation method. These irradiation methods enable a reduction of the amount of the treatment beam that strikes normal locations other than the affected area.

There are cases in which CT images of various respiratory phases are imaged immediately before treatment apart from use for treatment planning. In these cases, a CT image that is similar to CT image for treatment planning is selected from the CT images for the various respiratory phases. Irradiation is done automatically with the treatment beam when there is nearly coincidence of image information in the vicinity of thoracic diaphragm between the perspective image used for generating the selected CT image and the perspective image imaged during treatment.

With conventional techniques for automation, however, at the treatment stage or rehearsal stage, because treatment support is not provided by tracking the position of the patient, there have been cases in which the reliability was insufficient.

DETAILED DESCRIPTIONS

A medical image processing apparatus of an embodiment has acquisitor, a first landmark detector, and an estimator. The acquisitor acquires a perspective image of an object to be treated imaged by an imaging apparatus. The first landmark detector detects a position of a landmark that appears in the perspective image acquired by the acquisitor. The estimator, based on relationship information indicating a relationship between the position of landmark and the position of a target, estimates the position of the search-for location of the object to be treated from the position of the landmark detected by the first landmark detector.

A medical image processing apparatus, a treatment system, a medical image processing method, and a medical image processing program of an embodiment will be described below, with references made to the drawings.

First Embodiment

Figure 1:
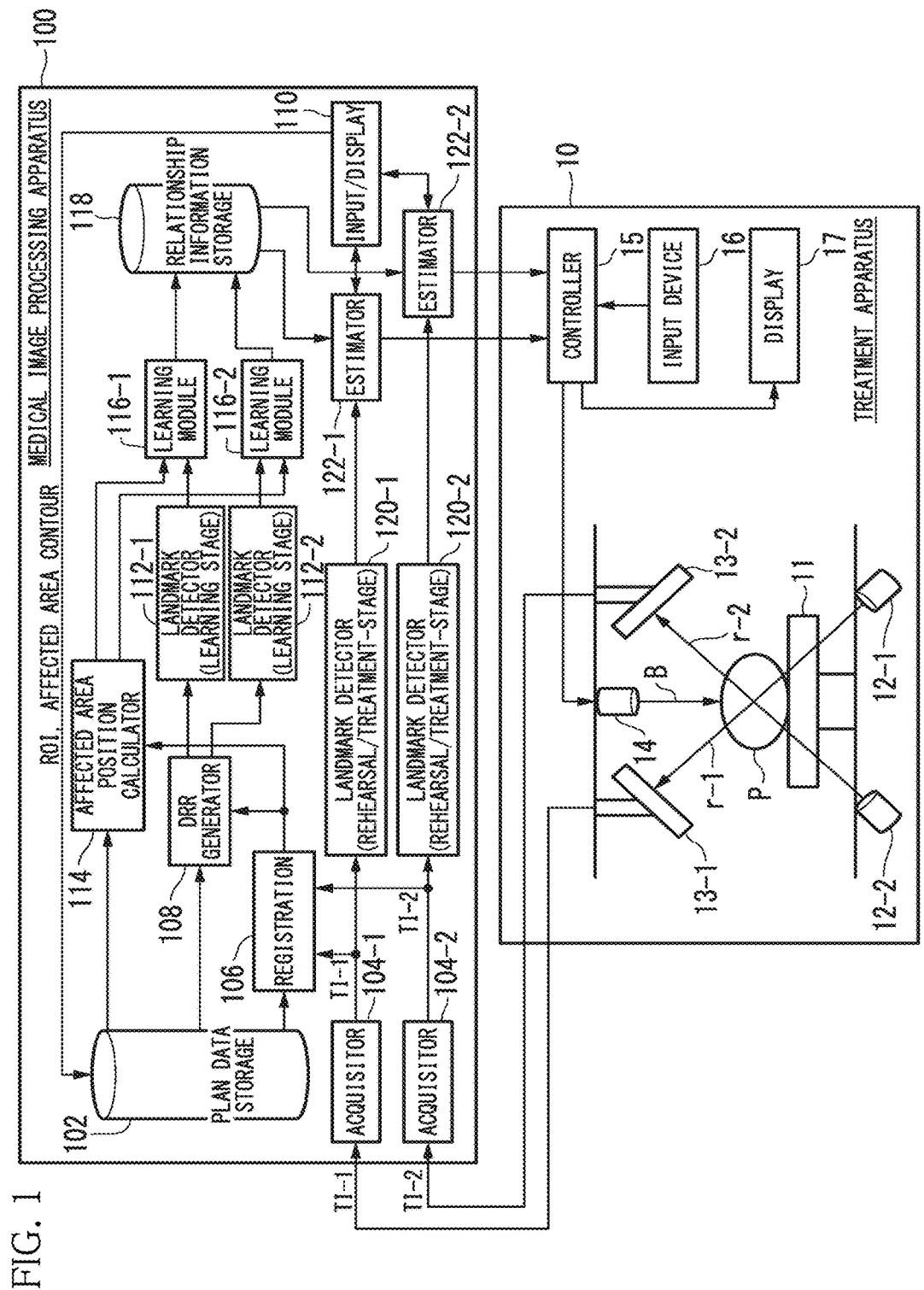
FIG. 1 shows an example of the constitution of a treatment system 1 that includes a treatment apparatus 10 and a medical image processing apparatus 100 of an embodiment.

FIG. 1 shows an example of the constitution of a treatment system 1 that includes a treatment apparatus 10 and a medical image processing apparatus 100 of an embodiment.

[Treatment Apparatus]

The treatment apparatus 10 has, for example, a bed 11, radiation sources 12-1 and 12-2, ray detectors 13-1 and 13-2, an irradiation port 14, a controller 15, an input device 16, and a display 17. In the following, the hyphens and the numerals thereafter indicate by which set of radiation sources and ray detector the ray for viewing or perspective image is generated.

The object to be treated (patient) P is fixed to the bed 11. The radiation sources 12-1 irradiates the object to be treated P with the ray for viewing r-2, and the radiation sources 12-2 irradiates the object to be treated P with the ray for viewing r-1 from an angle that is different from that of the radiation sources 12-1. The rays for viewing r-1 and r-2 are, for example, X-rays.

The ray for viewing r-1 is detected by the ray detector 13-1, and the ray for viewing r-2 is detected by the ray detector 13-2. The ray detectors 13-1 and 13-2 are, for example, flat panel detectors (FPDs), image intensifiers or color image intensifiers. The ray detector 13-1 detects and digitally converts the energy in the ray r-1 and outputs it to the medical image processing apparatus 100 as the perspective image TI-1. The ray detector 13-2 detects and digitally converts the energy in the ray r-2 and outputs it to the medical image processing apparatus 100 as the perspective image TI-2. Although FIG. 1 shows two sets of radiation sources and ray detectors, the treatment apparatus 10 may provide three or more sets of radiation sources and ray detectors.

At the treatment stage, the irradiation port 14 irradiates the object to be treated P with the treatment beam B. The treatment beam B includes, for example, an X-ray, a γ-ray, an electron beam, a proton beam, a neutron beam, or a heavy particle beam. Although FIG. 1 shows only one irradiation port 14, the treatment apparatus 10 may provide a plurality of irradiation gantries 14. Although FIG. 1 shows the irradiation port positioned vertically above the object to be treated P, the treatment apparatus 10 may provide an irradiation port horizontally with respect to the object to be treated P.

The controller 15 is implemented, for example, by a computer placed within a treatment room in which the treatment apparatus 10 is installed. The controller 15, in accordance with a treatment plan, controls the radiation sources 12-1 and the radiation sources 12-2 so as to irradiate with the rays for viewing r-1 and r-2. The input device 16, for example, is an input device such as dedicated keys, dials, a touch panel, a general-purpose keyboard, or a mouse. At the treatment stage, the controller 15 controls the irradiation port 14 so as to irradiate with the treatment beam B, in accordance with the treatment plan. The display 17 displays images and the like that are sent from the medical image processing apparatus 100.

[Medical Image Processing Apparatus]

The constitution of the medical image processing apparatus 100 will be described below. The medical image processing apparatus 100 has, for example, a plan data storage 102, acquisitors 104-1 and 104-2, a registrator 106, a DRR (digitally reconstructed radiograph) generator 108, an input/display 110, learning-stage landmark detectors 112-1 and 112-2, an affected area position calculator 114, learning modules 116-1 and 116-2, relationship information storage 118, rehearsal/treatment-stage landmark detectors 120-1 and 120-2, and estimators 122-1 and 122-2.

A part of these functional units are software functional units that function by execution of a program stored in a storage being executed by, for example, a processor such as a CPU (central processing unit) or GPU (graphics processing unit). A part or all of these functional units may be hardware functional units, such as an FPGA (field-programmable gate array), an LSI (large-scale integration) device, or an ASIC (application specific integrated circuit). The medical image processing apparatus 100 is connected to the treatment apparatus 10 by a LAN (local area network) or a WAN (wide area network). The acquisitors 104-1 and 104-2 include interfaces for connecting with a network. The plan data storage 102 and the relationship information storage 118 are implemented by storage devices such as a ROM (read-only memory), RAM (random-access memory), a HDD (hard-disk drive), or a flash memory. The program executed by a processor such as a CPU or GPU may be stored in a non-transitory computer readable storage medium of the medical image processing apparatus 100 beforehand, or may be downloaded via a network from another computer. A program stored in a removable non-transitory computer readable storage medium may be installed into the medical image processing apparatus 100.

Figure 2:
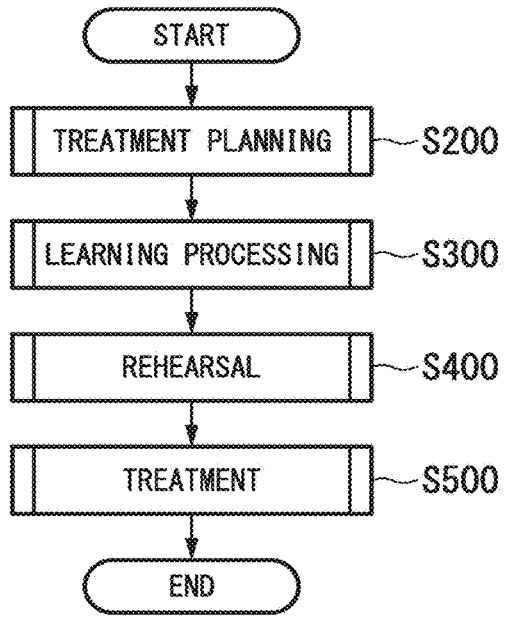
FIG. 2 shows a flowchart indicating the flow of treatment performed using the treatment system 1 according to a first embodiment.

The various functional units of the medical image processing apparatus 100 will now be described, with references made to the flow of treatment. FIG. 2 is an example of a flowchart, showing the flow of treatment performed using the treatment system 1 according to the first embodiment.

First, before performing treatment (for example, approximately one week before), a treatment plan is established (step S200). This will be described with reference to FIG. 3, which is an example of a flowchart showing the flow of the treatment planning.

First, at the treatment planning stage, a 4D CT image is done of the object to be treated P (step S202). Next, the 4D CT image is stored in the plan data storage 102 of the medical image processing apparatus 100 (step S204). The 4D CT image is the arrangement of n CT images, which are three-dimensional volume data, in a time sequence. The period of time obtained by multiplying the number n by the time interval of the time-sequence images is set, for example, so as to cover the time of variation of one cycle of respiratory phases. The number n is, for example, 10.

Next, of the n CT images, one CT image is, for example, displayed, and a contour input by the user is accepted with respect thereto (step S206). The user is, for example, a physician or a radiologic technologist using the medical image processing apparatus 100. At this step, the medical image processing apparatus 100 displays on the input/display 110 a cross-sectional image of the CT image with the object to be treated P having exhaled. The user uses the input/display 110 to input the contour of the lesion, which is the affected area, or organs that are not to be irradiated by the treatment beam B, while changing the cross-section that is displayed. The "affected area" is one example of a target area that the medical image processing apparatus 100 targets for estimation of position. The input/display 110 is, for example, a keyboard, a mouse, a touch panel, radio buttons or other input device and a display device such as an LCD or organic EL display device.

Next, the medical image processing apparatus 100 generates contour information and stores the contour information in the plan data storage 102 (step S208). At this step, the medical image processing apparatus 100 sets contours with respect to each of the (n−1) CT image other than the CT image in which the user input a contour at step S206 by deformable registration. In FIG. 1, the block that executes the deformable registration has been omitted.

Next, in the medical image processing apparatus 100, a treatment plan is proposed (step S210). Specifically, based on the contour information input and generated at step S206 and S208, a plan is made, based on gated irradiation or tracking irradiation treatment method, regarding from what direction, to where, and to what extent the treatment beam B is to be irradiated when a patient is in which position. This plan is proposed by a treatment planning program stored in the medical image processing apparatus 100. The proposed plan is displayed on the input/display 110 and verified by the user. The treatment plan information is, for example, stored in a storage of the controller 15. In FIG. 1, the block that proposes the plan has been omitted.

Figure 3:
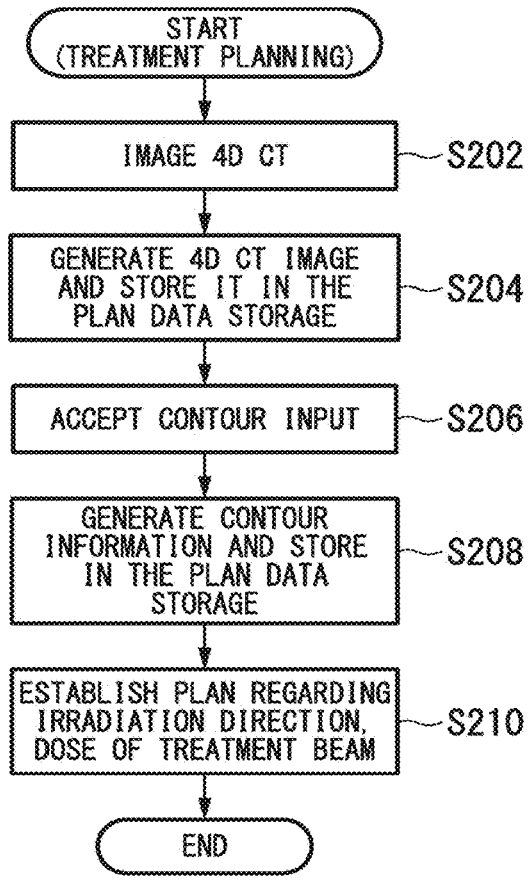
FIG. 3 shows a flowchart indicating the flow of treatment planning.

In the flowchart of FIG. 3, a part of the various processing described as the processing executed by the medical image processing apparatus 100 may be executed by an external device. For example, the processing to display the cross-sectional image of a CT image, the processing to receive input from a user related to a contour, the processing for executing deformable registration, and the processing for proposing a treatment plan may be executed by treatment planning apparatus that is external to the medical image processing apparatus 100.

When the treatment plan is proposed, the medical image processing apparatus 100 performs learning processing to learn the relationship between the position of the landmark of the object to be treated P and the position of the affected area (step S300). The learning processing is performed immediately before the rehearsal at step S400, on the same day as the treatment at step S500. If the treatment extends over a plurality of days, the learning may be performed on only the first day of treatment. The learning may alternatively be performed on a day different from the treatment and the rehearsal.

Figure 4:
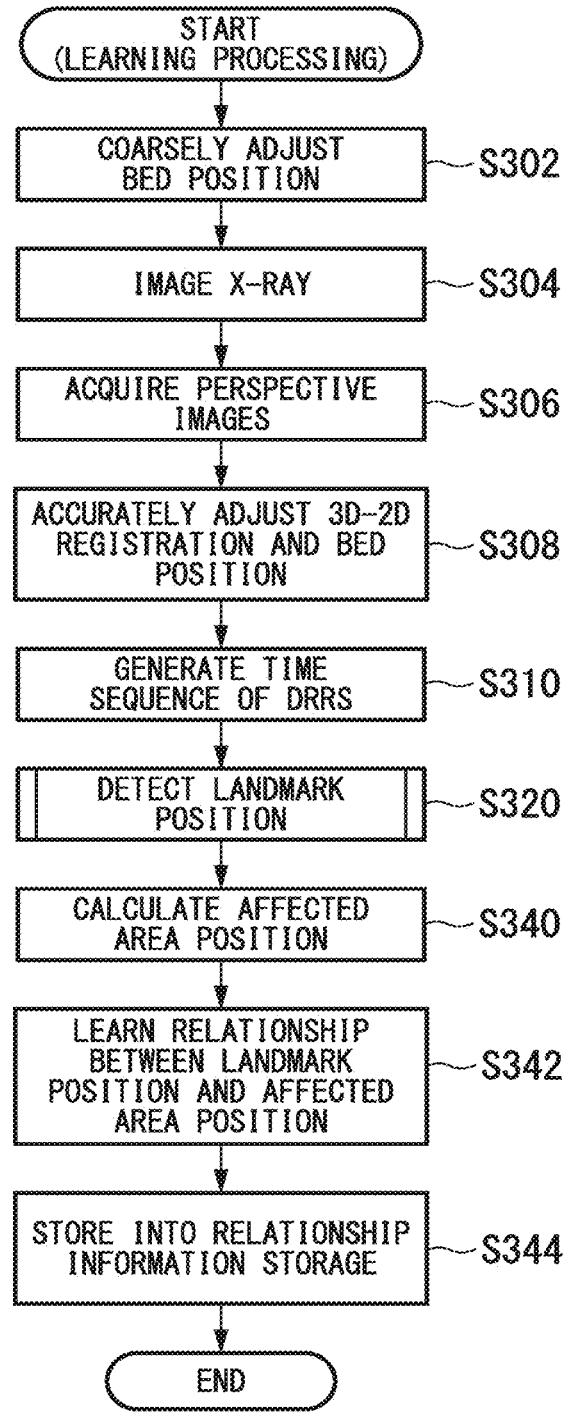
FIG. 4 shows a flowchart indicating the flow of learning processing.

At the learning processing stage, the object to be treated P is made to lie on the bed 11 and is held by a shell or the like. The processing is performed by the flow as shown in FIG. 4, which is an example of a flowchart showing the flow of learning processing.

First, a coarse adjustment is made of the position of the bed (step S302). At this stage, the user verifies the position and attitude of the object to be treated P by viewing and moves the bed 11 to a position at which it appears that the treatment beam B from the irradiation port 14 will strike the object to be treated P. This provides a coarse adjustment of the position of the bed 11.

Next, the perspective images TI-1 and TI-2 used for fine adjustment of the bed position are imaged (step S304). The perspective images TI-1 and TI-2 are imaged at the timing point at which, for example, the object to be treated P has exhaled, by the radiation sources 12-1 and ray detector 13-1 and the radiation sources 12-2 and ray detector 13-2, respectively. Because the position of the bed 11 has already been coarsely adjusted at step S302, the region of the affected area of the object to be treated P appears in the perspective images TI-1 and TI-2. The acquisitor 104-1 and the acquisitor 104-2 of the medical image processing apparatus 100 acquire the perspective images TI-1 and TI-2, respectively, and output them to the registrator 106 (step S306).

The registrator 106 then reads out from the plan data storage 102 the expiratory phase CT image of the 4D CT images, compares it with the perspective images TI-1 and TI-2 and, by 3D-2D registration, calculates information of the position and attitude of the object to be treated P on the bed 11 (step S308). The expiratory phase is the respiratory phase at which the object to be treated P has exhaled a breath completely. The 3D-2D registration is processing of calculating the position and attitude of the CT image data for which the picture angle of the DRR, which is a perspective image generated virtually by placing the CT image data virtually over the bed 11, coincides with the perspective images TI-1 and TI-2. This calculates the information of the position and attitude of the object to be treated P on the bed 11. Based on this position and attitude information, the position of the bed 11 is precisely adjusted either automatically or by a human operation. The position and attitude after the adjustment are output to the DRR generator 108 and the affected area position calculator 114.

Next, the DRR generator 108, based on the position and attitude information obtained at step S308, generates a time sequence of n DRRs from the 4D CT images (step S310). Because the position of the bed 11 has already been precisely adjusted at step S308, the picture angles of DRRs generated at this step coincide with the perspective images TI-1 and TI-2.

Next, the learning-stage landmark detectors 112-1 and 112-2 detect the position of the landmark that appears on the time sequence of DRRs generated at step S310, taking into account input from the input/display 110 (step S320).

[Landmark Detection]

The method of detecting the position of the landmark will now be described. The method adopted for detecting the position of the landmark may be used in common by the learning-stage landmark detectors 112-1 and 112-2 and the rehearsal/treatment-stage landmark detectors 120-1 and 120-2 (the types of input images being different). In the following, the numerals following the hyphens that indicate to which set of ray detector the generated perspective image corresponds are sometimes omitted.

The learning-stage landmark detector 112 detects, in one DRR selected from the time sequence of DRRs, the position of a landmark in an ROI (region of interest), within a region of interest ROI, or in the vicinity of a region of interest ROI, as specified by the user using the input/display 110.

Figure 5:
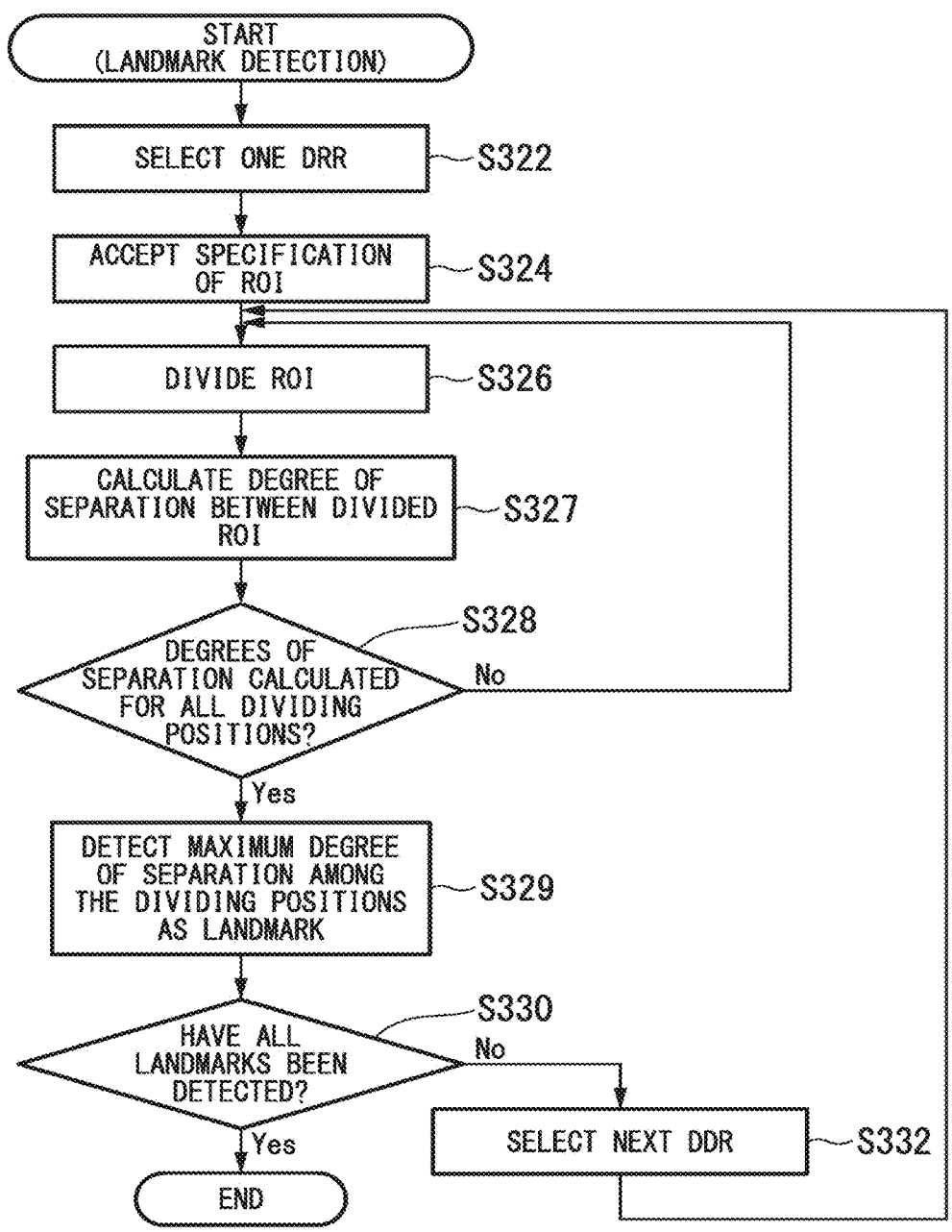
FIG. 5 shows a flowchart indicating the flow of processing executed by the learning stage landmark detector 112.
Figure 6:
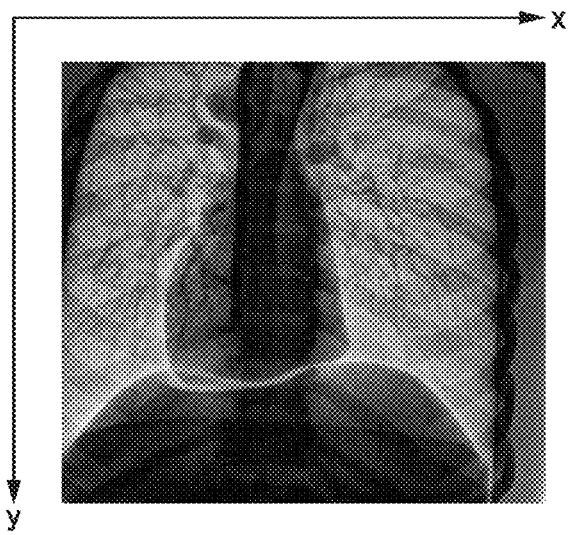
FIG. 6 shows an example of one selected DRR.

FIG. 5 is an example of a flowchart showing the flow of processing executed by the landmark detector 112 at the learning stage. First, the learning-stage landmark detector 112 selects one DRR from the time sequence of DRRs (step S322). The learning-stage landmark detector 112, for example, selects a DRR at a respiratory phase that is neither the expiratory phase nor the inspiratory phase. FIG. 6 shows an example of one selected DRR.

Figure 7:
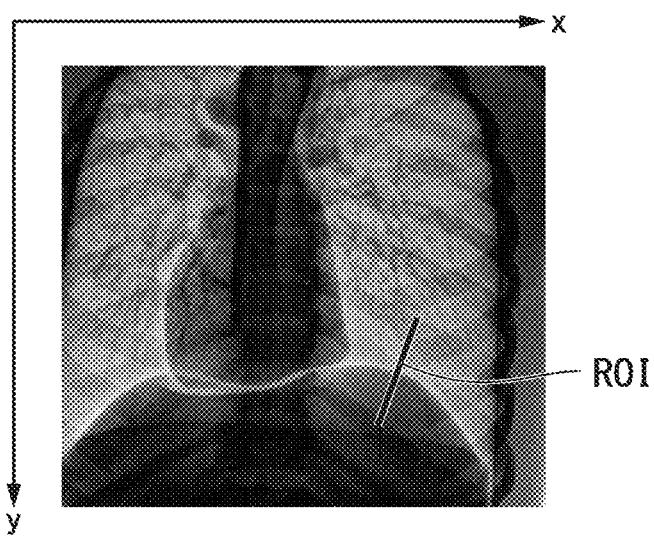
FIG. 7 shows an example of an ROI specified in the DRR.
Figure 8:
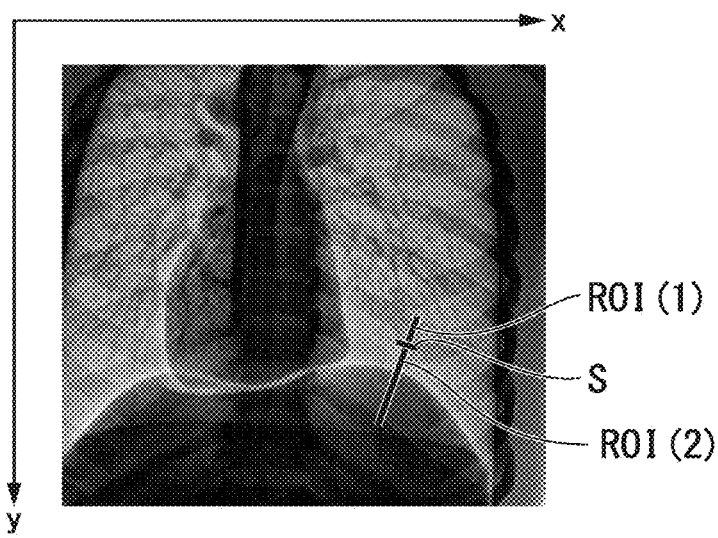
FIG. 8 shows the relationship between a dividing position S and the divided ROI(1) and ROI(2).
Figure 9:
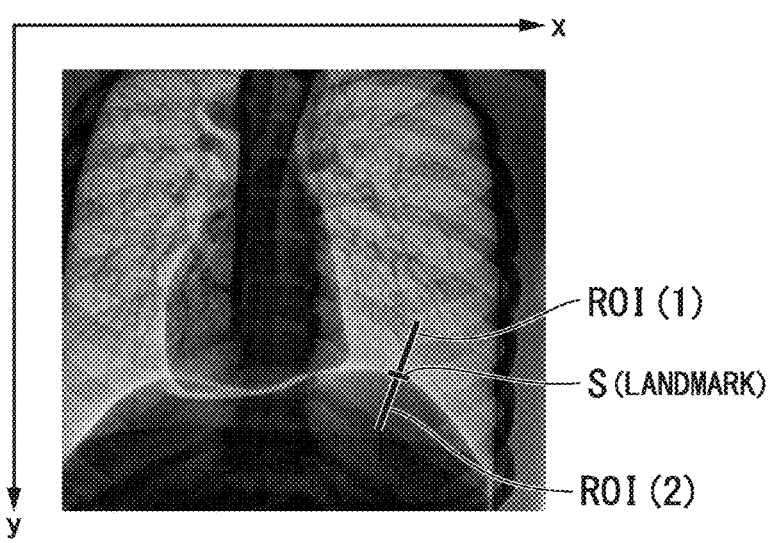
FIG. 9 shows a dividing position S detected as a landmark.

Next, the learning-stage landmark detector 112, while displaying the DRR on a display device of the display 110, accepts from the user specification of a region of interest (ROI) in the DRR (step S324). The ROI is geometric information used as the region for calculation when detecting the landmark from the input image, and is specified as line segments, regions, and other information. FIG. 7 shows an ROI specified in a DRR. In the example of FIG. 7, the ROI is specified as a line segment. In FIG. 7 through FIG. 9, the description is for the example of detection of the thoracic diaphragm as the landmark, and examples detection of the landmark will be described later.

The user uses, for example, radio buttons, to select whether the shape of the ROI is to be made a line segment or a rectangle, and the input is accepted by the input/display 110. The user then, for example, operates a mouse while viewing the DRR to specify the ROI by a dragging operation. The learning-stage landmark detector 112 applies the ROI specified at step S324 in the same manner to DRRs other than the DRR selected at step S322 from the time sequence of DRRs.

Next, the learning-stage landmark detector 112 changes the dividing position, for example at a prescribed width step, to divide the ROI into two (step S326). FIG. 8 shows the relationship between the dividing position S and the divided ROI(1) and ROI(2).

The learning-stage landmark detector 112 calculates the degree of separation between the divided ROI(1) and ROI(2) by the density values (step S327). The degree of separation is, for example, the difference between the average values of density of the ROI(1) and ROI(2). A judgment is then made as to whether or not the degrees of separation have been calculated for all of the dividing positions S changed by a prescribed width step (step S238). If all had not been calculated, return is made to step S326. If all calculations have been made, processing proceeds to step S329. At step S329, the dividing position S at which the degree of separation is maximum among the degrees of separation calculated at the various dividing positions S is detected as the landmark. FIG. 9 shows the dividing position S detected as the landmark. The position of the landmark can be, for example, expressed in the coordinate system of the input image. The position of the landmark may be expressed as the coordinates (x, y), or may be expressed by only an x coordinate or only a y coordinate. The position of the landmark may be presented as a line segment or as a region or the like. Another method of detecting the landmark will be described later.

The learning-stage landmark detector 112 judges whether or not the landmarks have been detected regarding all the DRRs (step S330). If the landmarks have not been detected for all the DRRs, the learning-stage landmark detector 112 selects the next DRR (step S332) and executes the processing starting at step S326). With regard to the ROI, the first one that has been specified at step S324 may be applied to all the DRRs. When the landmarks have been detected for all of the DRRs, the processing of this flowchart is ended.

When the position of a landmark is detected, the affected area position calculator 114, based on the affected area contour information stored in the plan data storage 102 and the position and attitude information obtained at step S308, calculates the affected area positions in the time sequence DRRs (step S340 in FIG. 4). The affected area position calculator 114, for example, assumes that the affected area mass for each of n CT images is the same, and calculates the three-dimensional position of the center of gravity from the contour information, and takes the corresponding position of the calculated center of gravity projected onto the DRR as the position of the affected area.

In this manner, a plurality of images (time-sequenced DRRs) having the same picture angle as the perspective image TI are images generated from a three-dimensional volume data movie, and by the affected area position calculator 114 developing information specified by the user regarding three-dimensional volume data having at least one respiratory phase of a movie of three-dimensional volume data into images for other respiratory phases, the position of the affected area of the object to be treated P in the plurality of images having the same picture angle as the perspective image TI is derived.

[Relationship Information Learning]

Next, the learning module 116 learns (step S342) the relationship between the position of the landmark in a DRR detected at step S320 and the position of the affected area in the DRR calculated at step S340. The learning module 116 stores the learned relationship into the relationship information storage 118 as relationship information (step S344). The learning module 116 may be omitted from the present embodiment.

The method of learning the relationship is will now be described. As described above, the medical image processing apparatus 100 has an input/display 110 that accepts input operations by a user, a learning-stage landmark detector 112 that detects the position of a landmark in a plurality of images (time-sequenced DRRs) having the same picture angle as a perspective image TI within an affected area or in the vicinity of an affected area specified by the user using the input/display 110, and the learning module 116 acquires from the learning-stage landmark detector 112 the positions of a plurality of landmark in a plurality of images for differing respiratory phases.

This description will be for the case in which the position of the landmark obtained by the time sequence is a part of the thoracic diaphragm and the heart wall contour, and the information used in the learning of the correspondence relationship is the y coordinate of the thoracic diaphragm and the x coordinate of the heart wall. The use of the y coordinate of the thoracic diaphragm and the x access of the heart wall in learning the correspondence relationship is done because, for example if the affected area is the lung, the main amounts of movement of the affected area is represented by the amount of movement of in the y direction in accordance with the movement of the thoracic diaphragm in the y direction by respiration and the amount of movement in the x direction in accordance with the movement of the heart wall in the x direction by the heartbeat.

Figure 10:
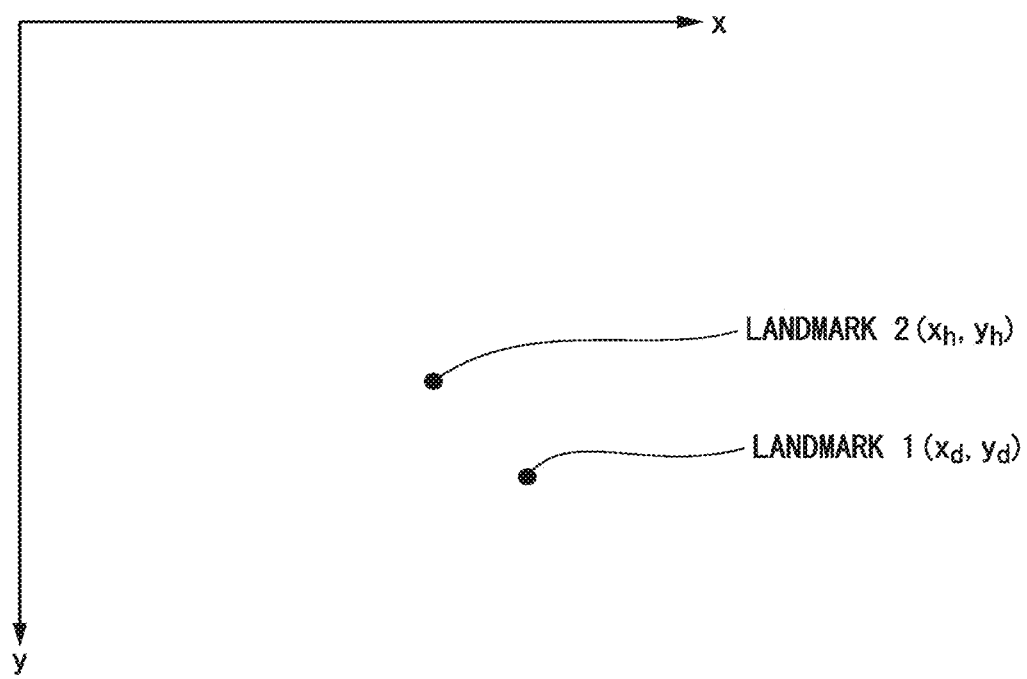
FIG. 10 shows a landmark 1 on the contour of the thoracic diaphragm and a landmark 2 on the contour of the heart wall.

FIG. 10 shows a landmark 1 on the contour of the thoracic diaphragm and a landmark 2 on the contour of the heart wall. In this drawing, the coordinates of the landmark 1 are represented as $(x_d, y_d)$ and the coordinates of the landmark 2 are represented as $(x_h, y_h)$. In the following, the y coordinates of the thoracic diaphragm obtained in a time sequence are represented as $y_d(p)$ and the x coordinates of the heart wall obtained in a time sequence are represented as $x_h(p)$. In this case, p is an index indicating to which of then DRRs the value is related, wherein p=0, 1, . . . , n−1. Because each of the time-sequenced DRRs corresponds to a respiratory phase, there are cases in which this is represented as the respiratory phase p. The positions of the affected area obtained by the time sequence are represented as $(x_t(p), y_t(p))$.

Figure 11:
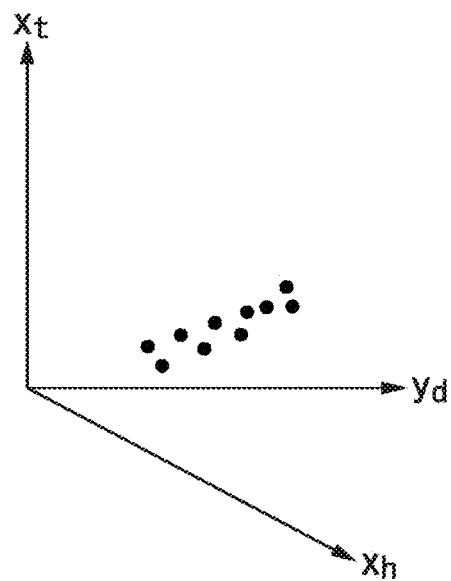
FIG. 11 shows one aspect of the relationship between the position of a landmark and the position of an affected area.

By defining $y_d(p)$, $x_h(p)$ and $(x_t(p), y_t(p))$ in this manner, if a three-dimensional profile is created with the coordinates $(x_h, y_d, x_t)$ for all the indices p, the result is, for example, as shown in FIG. 11. FIG. 11 shows one aspect of the relationship between the position of a landmark and the position of an affected area.

Figure 12:
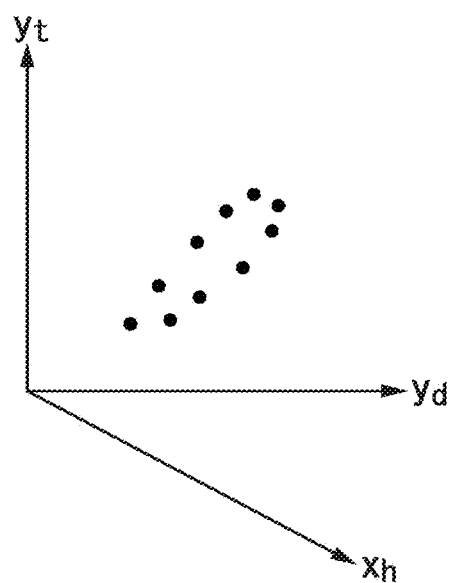
FIG. 12 shows another aspect of the relationship between the position of a landmark and the position of an affected area.

Also, if a three-dimensional profile is created with the coordinates $(x_h, Y_d, Y_t)$ for all of the indices p, the result is, for example, as shown in FIG. 12. FIG. 12 shows another aspect of the relationship between the position of a landmark and the position of an affected area.

The learning module 116, based on the trends represented by FIG. 11 and FIG. 12, creates as relationship information, for example, a function f that, upon inputting the y coordinate $y_d$ of the thoracic diaphragm and the x coordinate $x_h$ of the heart wall, returns the x coordinate $x_t$ of the affected area, and a function g that, upon inputting the y coordinate $y_d$ of the thoracic diaphragm and the x coordinate $x_h$ of the heart wall, returns the y coordinate $y_t$ of the affected area (refer to Equation (1) and Equation (2)). Although the learning module 116 creates the functions f and g as relationship information in this case, it may create as relationship information table data, a map, or some other information indicating the relationship between the position of the landmark and the position of the affected area.

[Equations 1, 2]

$$x_t = f(x_h, y_d) \quad (1)$$

$$y_t = g(x_h, y_d) \quad (2)$$

In this case, if the function model is made a second-order polynomial, it is possible to group Equation (1) and Equation (2) so as to represent them as Equation (3). In these equations, A is a 2-row, 6-column matrix of coefficients.

[Equation 3]

$$\begin{pmatrix} x_t \\ y_t \end{pmatrix} = A \begin{pmatrix} x_h^2 \\ y_d^2 \\ x_h y_d \\ x_h \\ y_d \\ 1 \end{pmatrix} \quad (3)$$

The learning module 116, for example, the point coordinate groups represented in FIG. 11 and FIG. 12, learns the coefficient matrix A as training data, using a statistical method such as the method of least squares. Specifically, the learning module 116 learns the coefficient matrix A by determining the coefficient matrix A that makes the squared error E represented by Equation (4) minimum.

[Equation 4]

$$E = \sum_{p=0}^{n-1} \left\| A \begin{pmatrix} x_h^2(p) \\ y_d^2(p) \\ x_h(p)y_d(p) \\ x_h(p) \\ y_d(p) \\ 1 \end{pmatrix} - \begin{pmatrix} x_t(p) \\ y_t(p) \end{pmatrix} \right\|^2 \quad (4)$$

The learning module 116 may alternatively learn the coefficient matrix A that minimizes the square error E represented by the Equation (5) by evaluating the coefficient matrix A. In this equation, w(p) is a weighting coefficient regarding the respiratory phase, wherein the closer p is to the expiratory phase, the larger is the value of w(p). This enables the determination of a coefficient matrix A such that the error is made small, particularly in the expiratory phase. The learning by Equation (5) is effective when using gated irradiation in the expiratory phase as the treatment method. In the landmark detection stage, w(p) may be set so as to take a larger value, the greater is the degree of separation. This enables learning of the coefficient matrix A, having made the weights of DRRs with reliable detection results of the time-sequenced DRRs larger, thereby enabling improvement of the learning accuracy.

[Equation 5]

$$E = \sum_{p=0}^{n-1} w(p) \left\| A \begin{pmatrix} x_h^2(p) \\ y_d^2(p) \\ x_h(p)y_d(p) \\ x_h(p) \\ y_d(p) \\ 1 \end{pmatrix} - \begin{pmatrix} x_t(p) \\ y_t(p) \end{pmatrix} \right\|^2 \quad (5)$$

As described above, the learning module 116 acquires the positions of a plurality of landmarks in a plurality of images (DRRs) for differing respiratory phases and, based on the positions of the plurality of landmarks and on the plurality of positions of the affected area in respiratory phases corresponding to the plurality landmarks, learns relationship information indicating the relationship between the landmark positions and the position of the affected area of the object to be treated P.

[Rehearsal]

When the learning processing ends, rehearsal is done (step S400 in FIG. 2). In the rehearsal, verification is made as to whether or not the affected area of the object to be treated P can tracked with a movie of the perspective image TI. The rehearsal is performed immediately before and on the same day as the treatment of step S500. If the treatment extends over a plurality of days, the rehearsal may be performed on only the first day of the treatment. Although the positioning of the object to be treated P is done immediately before the rehearsal, in the present embodiment, because the positioning of the object to be treated P has already been done, it is not necessary to perform the positioning anew.

Figure 13:
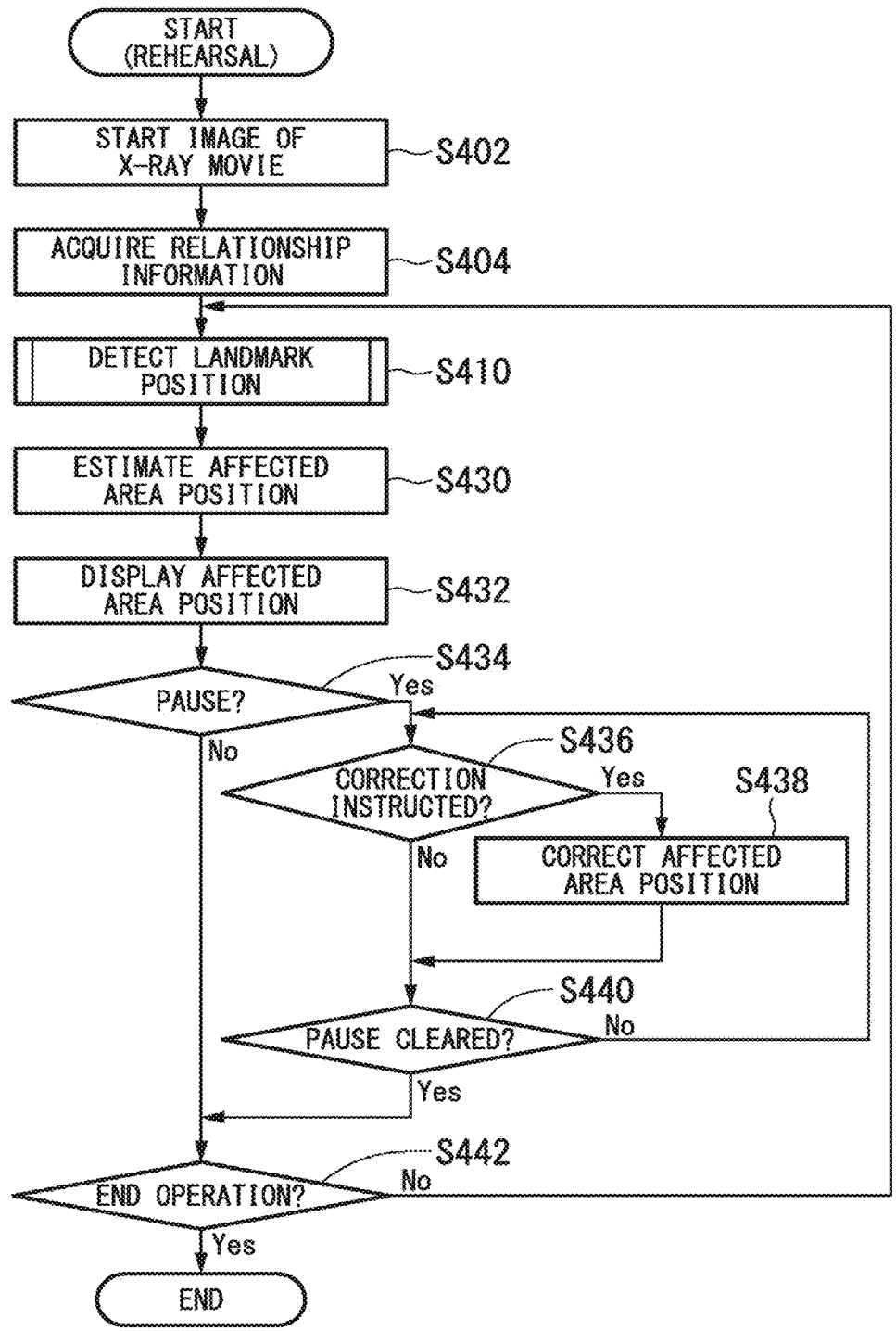
FIG. 13 shows a flowchart indicating the flow of processing performed in a rehearsal.

FIG. 13 is an example of a flowchart showing the flow of processing performed in a rehearsal. In the rehearsal, first, the image of a movies of the perspective images TI-1 and TI-2 (for example, X-ray movies) by the set of the radiation sources 12-1 and ray detector 13-1 and the set of the radiation sources 12-2 and ray detector 13-2 is started (step S402). Each frame of the movie is sequentially acquired as the perspective images TI-1 and TI-2 by the acquisitors 104-1 and 10402, and sequentially output to the rehearsal/treatment-stage landmark detectors 120-1 and 120-2. In the following description, the numerals following the hyphens are omitted.

Next, the estimator 122 reads out the relationship information learned in the learning processing from the relationship information storage 118 (step S404).

Figure 14:
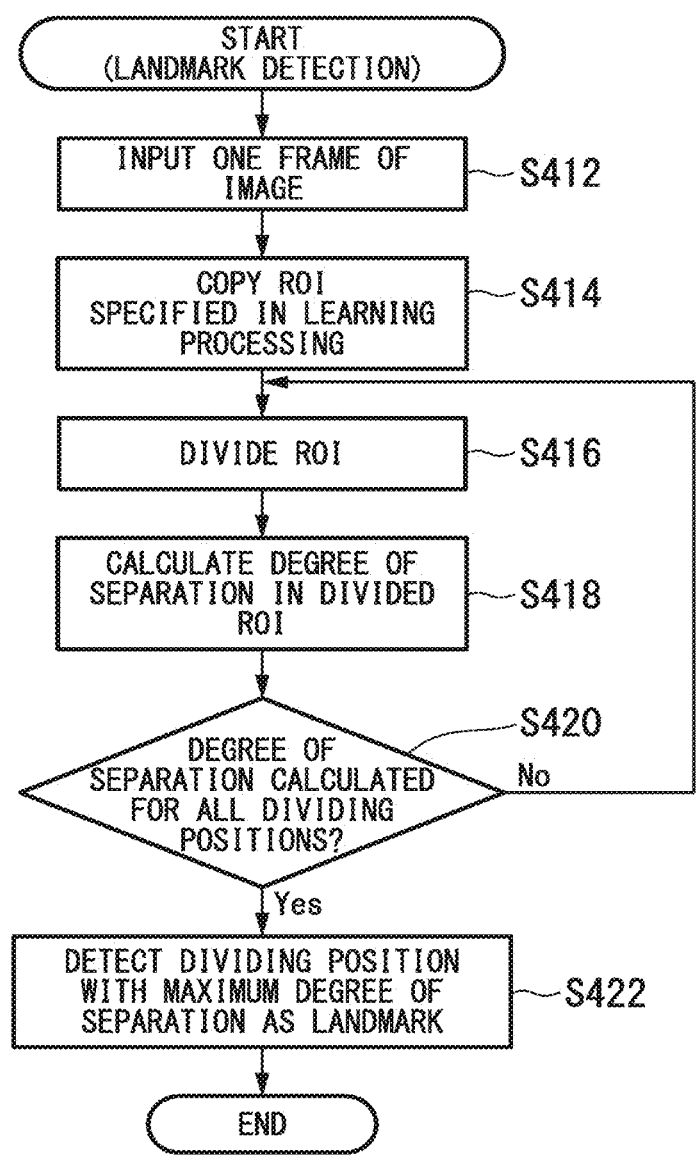
FIG. 14 shows a flowchart indicating the flow of processing executed by the rehearsal/treatment stage landmark detector 120.

Next, the rehearsal/treatment-stage landmark detector 120 detects the position of the landmark (step S410). This will be described below, with reference made to FIG. 14. FIG. 14 is an example of a flowchart indicating the flow of processing executed by the rehearsal/treatment-stage landmark detector 120.

First, one frame of the perspective image TI is input to the rehearsal/treatment-stage landmark detector 120 (step S412). Next, the rehearsal/treatment-stage landmark detector 120 copies the region of interest specified in the learning processing (step S414). Then, the rehearsal/treatment-stage landmark detector 120, similar to the learning-stage landmark detector 112, changes the dividing position, for example at a prescribed width step, to divide the ROI into two (step S416), and calculates the degree of separation from the density values of the divided ROI(1) and ROI(2) (step S418). A judgment is then made as to whether or not the degrees of separation have been calculated for all the dividing positions S changed by a prescribed width step (step S420). If all had not been calculated, return is made to step S416. If all calculations have been made, processing proceeds to step S422. At step S422, the dividing position S at which the degree of separation is maximum among the degrees of separation calculated at the various dividing positions S is detected as the landmark.

When the position of the landmark is detected, the estimator 122, based on the position of the landmark and the relationship information, estimates the position of the affected area of the object to be treated P (step S430 in FIG. 13). As described above, for example, the relationship information includes the function f that returns the x coordinate $x_t$ of the affected area if, for example, the y coordinate $y_d$ of the thoracic diaphragm and the x coordinate $x_h$ of the heart wall are input and the function g that returns the y coordinate $y_t$ of the affected area if the y coordinate $y_d$ of the thoracic diaphragm and the x coordinate $x_h$ of the heart wall are input. The estimator 122 inputs the y coordinate $y_d$ of the thoracic diaphragm and x coordinate $x_h$ of the heart wall detected by the rehearsal/treatment-stage landmark detector 120 into these functions as the input values, thereby estimating the x coordinate $x_t$ and the y coordinate $y_d$ of the affected area. The affected area may be a point, a two-dimensional region, or a three-dimensional region. In the example below, the description will be for the case of the affected area being a point.

Figure 15:
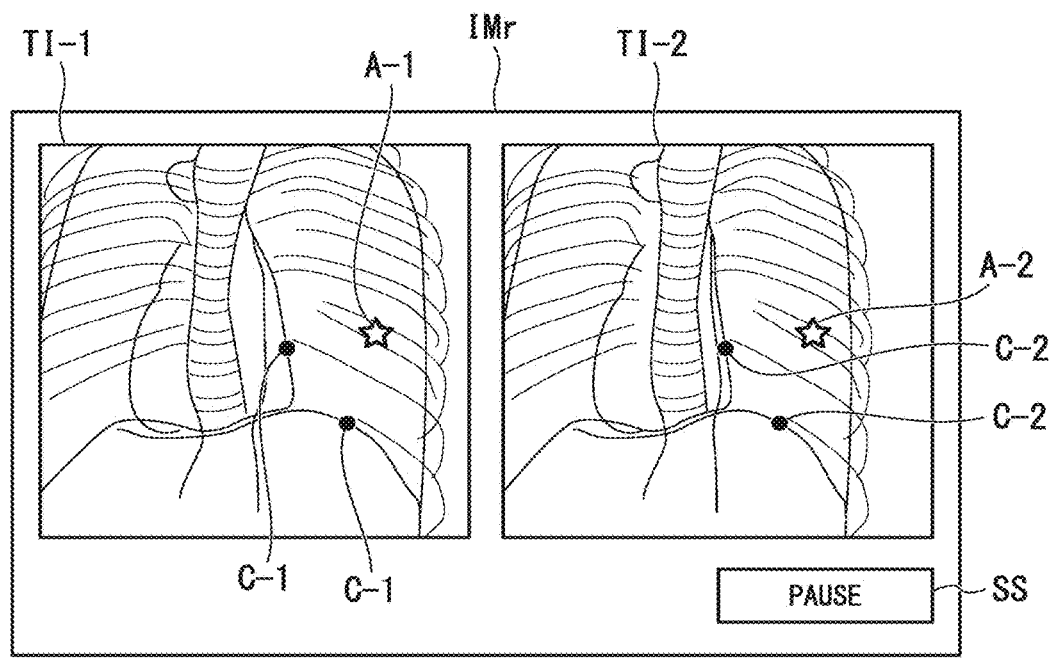
FIG. 15 shows an example of a display screen IMr at the rehearsal stage.

Next, the estimator 122 superimposes the estimated position of the affected area onto the perspective image TI and displays these on the display device of the input/display 110 (step S432). FIG. 15 shows an example of a display screen IMr. As illustrated, in the display screen IMr at the rehearsal stage, the perspective images TI-1 and TI-2 are, for example, displayed next to each other. The perspective images TI are displayed with the symbols A-1 and A-2, which indicate the positions of the affected area, and the symbols C-1 and C-2, which indicate the landmark that are the basis for estimating the position of the affected area superimposed thereon. In this manner, the estimator 122 controls the display device of the input/display 110 so that the symbols indicating the estimated position of the affected area are displayed superimposed onto the perspective images TI. Because the display screen IMr is, for example, repeatedly updated by loop processing (step S410 to S442) in the flowchart of FIG. 13, it appears to the user to be a displayed movie of the perspective image TI indicating the position of the landmark and the position of the affected area. The display screen IMr is provided with a pause switch SS that is a GUI switch that gives an instruction to stop the movie temporarily.

Having recognized this display screen IMr, the user can verify whether or not the position of the affected area, in which the user has verified on the perspective images TI-1 and TI-s from the two directions by viewing her/himself, coincides with the symbols A-1 and A-2 that indicate the position of the affected area displayed as the estimation results. This enables improvement of the reliability of treatment.

Next, the medical image processing apparatus 100 judges whether or not the pause switch SS has been operated (step S434). If the pause switch SS has been operated, the medical image processing apparatus 100 judges whether or not a correction instruction has been made (step S436). A correction instruction is made, for example, by the user clicking the correct position of the affected area with a mouse. If a correction instruction has been made, the estimator 122 corrects the position of the affected area (step S438). A correction instruction may be made with respect to either one or both of the perspective images TI-1 and TI-2. The estimator 122, for example, determines the difference between an symbol that had been displayed and the position at which the correction instruction has been made as the correction amount, after which, when estimating the position of the affected area, the correction amount is accounted for when establishing the estimation results. The correction amount is inherited by the treatment stage as well. The estimator 122, based on the difference, may also correct the relationship information itself. This also corrects the position of the symbol that had been displayed. That is, the medical image processing apparatus 100 has a pause switch SS on its input/display 110, which accepts operations to correct the position of the symbol, and the input/display 110 displays the symbol that has had its position corrected in accordance with the correction operations superimposed on the perspective image TI.

Correction instructions are accepted (step S440) until the pause switch SS is operated again to clear the paused condition. The medical image processing apparatus 100 continues the movie display on the display screen IMr until the user gives an end instruction (step S442).

This control enables the user to verify the position of the affected area used in control of the irradiation port 14 by the treatment system 1 in the treatment stage. There may be cases in which it is difficult to directly determine the position of the affected area on the perspective image TI. Given this, in the medical image processing apparatus 100 of the present embodiment, first the relationship between the position of at least one landmark of the thoracic diaphragm, the heart wall, the thoracic wall of the object to be treated, or a bone and the position of the affected area is determined on the DRR, and the position of the affected area is reproduced from the position of the landmark on the perspective image TI. That is, the medical image processing apparatus 100 of the present embodiment estimates the position of the affected area, based on the position of the landmark that can be recognized by computer processing, on the perspective image TI as well, and the above-noted relationship. This enables a verification, at the rehearsal stage or treatment stage, of whether or not the position of the affected area matches the intention of the user.

[Treatment Stage]

In the rehearsal, when the position of the affected area is verified and corrected, the treatment starts (step S500 in FIG. 2). In the treatment stage, the treatment beam B irradiates the affected area of the object to be treated P. Although the object to be treated P is positioned immediately before the treatment stage, in the present embodiment because the positioning of the object to be treated P has already been done, it is not necessary to perform the positioning anew.

Figure 16:
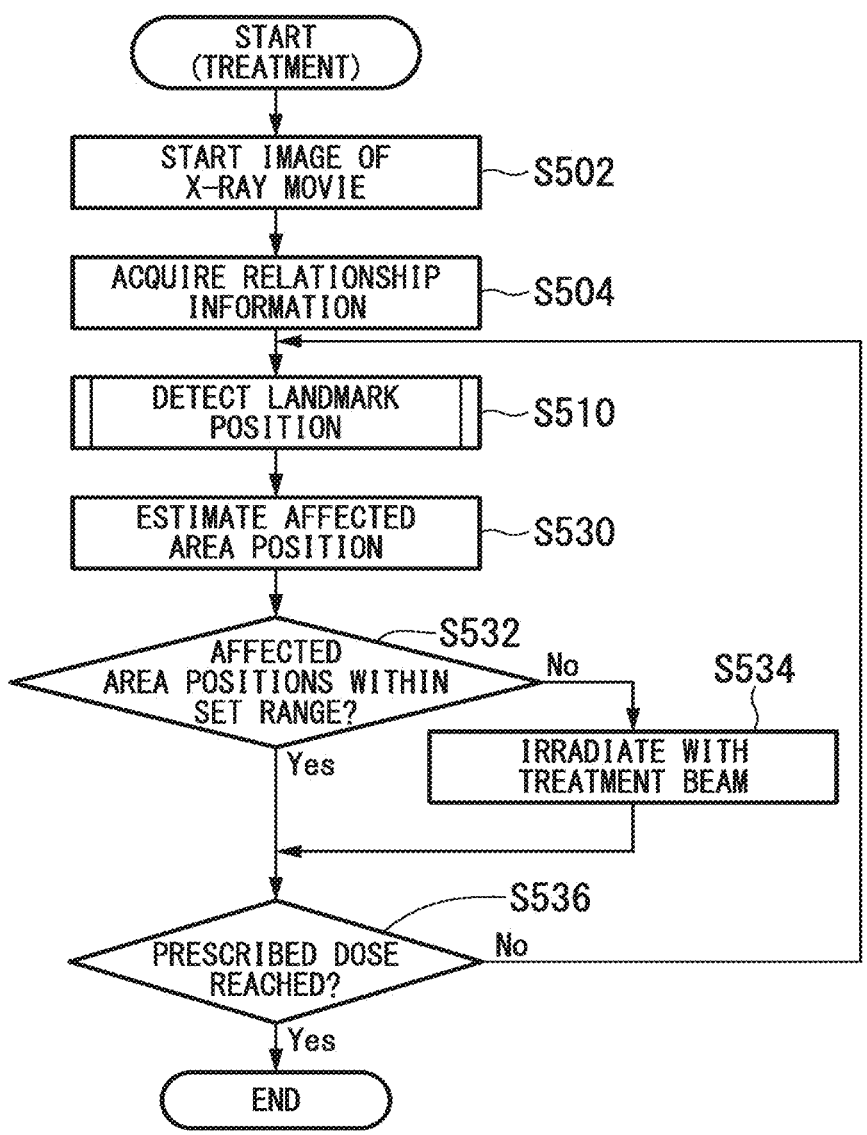
FIG. 16 shows a flowchart indicating the flow of processing performed at the treatment stage.

FIG. 16 is an example of a flowchart showing the flow of processing performed in treatment. First, similar to the rehearsal stage, the capturing of the perspective images TI-1 and TI-2 starts (step S502), for example, as an X-ray movie. Next, the estimator 122 reads relationship information learned in the learning processing from the relationship information storage 118 (step S504).

Next, the rehearsal/treatment-stage landmark detector 120 detects the position of the landmark (step S510). The processing to detect the position of the landmark is, for example, the same as the processing described regarding FIG. 14. When the position of the landmark is detected, the estimator 122, based on the position of the landmark and the relationship information, estimates the position of the affected area of the object to be treated P (step S530). Specifically, the estimator 122 applies the function f to the input y coordinate $y_d$ of the thoracic diaphragm and the x coordinate $x_h$ of the heart wall to derive the x coordinate $x_t$ of the affected area and applies the function g to the y coordinate $y_d$ of the thoracic diaphragm and the x coordinate $x_h$ of the heart wall to derive the y coordinate $y_t$ of the affected area.

Next, the controller 15 of the treatment apparatus 10 judges whether or not the position of the affected area estimated at step S530 is within a range that has been set beforehand (step S532). If the position of the affected area is within the range set beforehand, the controller 15 controls the irradiation port 14 so as to irradiate with the treatment beam B (step S534). If the position of the affected area is outside the range set beforehand, the controller 15 does not make the irradiation port 14 irradiate with the treatment beam B. This treats the affected area of the object to be treated P by the gated irradiation method.

The processing of step S510 to S534 is controlled so that when the accumulated dose of the treatment beam B irradiated on the affected area reaches a pre-established amount the processing is completed (step S536). Although this has been the flow of gated irradiation treatment, the tracking irradiation method can be implemented by tracking by estimation of the position of affected area in the movie and then by irradiating that position of the affected area using the treatment beam B.

The "position of the affected area" at the treatment stage is first determined as coordinates in the perspective images TI-1 and TI-2, and the "position of the affected area" that is subject to processing of judgment at step S532 may be a three-dimensional position. The set range may be set as a range in the perspective images TI-1 and TI-2, or may be set as range in a three-dimensional world. In the latter case, the learning module 116 may learn the relationship between the position of the landmark on the two images and the three-dimensional position of the affected area. In this case, the estimator 122 is integrated as one constituent element. Each of the estimators 122-1 and 122-2 may have a function of deriving the three-dimensional position of the affected area, based on the positions that each estimates as the position of the affected area.

Figure 17:
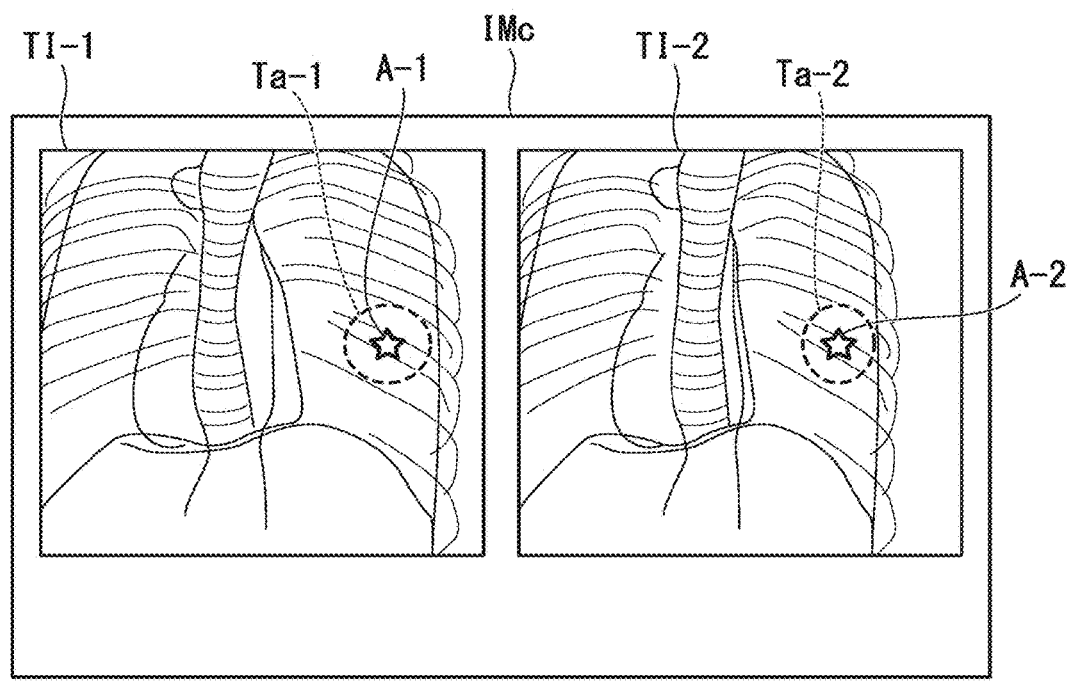
FIG. 17 shows an example of a display screen IMc at the treatment stage.

In the treatment stage, the treatment system 1 may display on the display 17 a display screen enabling comparison of the position of the affected area with the set range. FIG. 17 shows an example of the display screen IMc at the treatment stage. As shown in drawing, in the display screen IMc, the setting range Ta-1 corresponding to the perspective image TI-1 and the object A-1 indicating a position of the affected area corresponding to the perspective image TI-1 can be compared. Also in the display screen IMc, the set range Ta-2 corresponding to the perspective image TI-2 and the object A-2 indicating a position of the affected area corresponding to the perspective image TI-2 can be compared.

By this control, the medical image processing apparatus 100 of the present embodiment can improve the reliability of treatment. Conventionally, control has been performed so that irradiation is done with a treatment beam based on image information in the vicinity of the thoracic diaphragm in a perspective image imaged at the treatment stage. With this conventional method, however, because treatment support is not provided by tracking the position of the affected area, there may be cases in which the reliability of the treatment is insufficient. In contrast, the medical image processing apparatus 100 of the present embodiment, by estimating the position of the affected area from the perspective image TI, based on the relationship between the position of the landmark and the position of the affected area, can improve the reliability of treatment.

The medical image processing apparatus 100 of the present embodiment can also improve the energy efficiency of treatment. Conventionally, separate from the treatment planning image immediately before treatment, the task of capturing images at various respiratory phases and of selecting an image of a desired respiratory phase has been performed, thereby placing a burden on the user. In contrast, the medical image processing apparatus 100 of the present embodiment, by learning the relationship between the position of a landmark and the position of the affected area, eliminates the above-noted task and improves the energy efficiency of treatment.

The above-described medical image processing apparatus 100 according to the first embodiment, by having a rehearsal/treatment-stage landmark detector 120 that detects the position of a landmark in a perspective image and an estimator 122 that estimates the position of the affected area of the object to be treated P from the position of the landmark detected by the rehearsal/treatment-stage landmark detector 120, based on relationship information indicating the relationship between the position of the landmark and the position of the affected area, it is possible to improve the reliability of treatment.

Also, the medical image processing apparatus 100 according to the first embodiment, by controlling the display 17 so that the object A indicating the position of the affected area of the object to be treated P estimated by the estimator 122 is displayed superimposed on the perspective image TI, can further increase the reliability of treatment.

Also, according to the medical image processing apparatus 100 of the first embodiment, in a condition in which the object A indicating the position of the affected area of the object to be treated P is superimposed on the perspective image TI, if the user makes an instruction to the input/display 110 to correct the position of the affected area of the object to be treated P, because in the following processing the estimation of the position of the affected area of the object to be treated P reflects the correction amount made by the correction instruction, not only is convenience improved, but the reliability of the treatment is further improved.

The medical image processing apparatus 100 according to the first embodiment has a learning-stage landmark detector 112 that detects a position of a landmark in a plurality of DRRs of different respiratory phases and that have the same picture angle as the perspective image TI and a learning module 116 that learns the relationship information based on the position of the landmark detected in the plurality of DRRs by the learning-stage landmark detector 112 and on the position of the affected area of the object to be treated P in the plurality of DRRs, thereby enabling it to improve the energy efficiency of treatment.

According to the medical image processing apparatus 100 of the first embodiment, because the learning-stage landmark detector 112 detects the position of the landmark in a plurality of DRRs within a ROI specified using the input/display 110 by a user, it is possible to reduce the burden of computer processing required to detect the position of the landmark.

The above-noted treatment system 1 has the medical image processing apparatus 100, the radiation sources (irradiation port 14) that irradiates the object to be treated P with the treatment beam B, and the controller 15 that controls the radiation sources so that it irradiates with the treatment beam B if the position of the affected area of the object to be treated P estimated by the estimator 122 is within the set range.

The medical image processing apparatus 100 has acquisitors 104-1 and 104-2 that acquire perspective images of an object to be treated imaged by an imaging apparatus, a processor such as a CPU or GPU, and a storage device such as a ROM or RAM, an HDD, or flash memory. A program is stored in a storage device to cause the processor to function as the rehearsal/treatment-stage landmark detectors 120-1 and 120-2 that detect the positions of the landmark that appears in the perspective images acquired by the acquisitors 104-1 and 104-2, and the estimators 122-1 and 122-2 that, based on relationship information indicating the relationship between the landmark position and the affected area position, estimate the position of the affected area of the object to be treated P from the position of the landmark detected by the rehearsal/treatment-stage landmark detectors 120-1 and 120-2.

The medical image processing apparatus 100 has a processor such as a CPU or GPU and a storage device such as a ROM or RAM, an HDD, or flash memory. A program is stored in the storage device to cause the processor to acquire positions of a plurality of landmarks in a plurality of images of different respiratory phases and, based on the plurality of positions of the affected area in respiratory phases corresponding to the plurality of landmarks and the plurality of positions of the landmark, to function as learning module that learns the relationship information indicating the relationship between the position of the landmark and the position of the affected area of the object to be treated P.

Variation Example

As long as the nature of each of the steps in the flowcharts given as examples in the above-noted embodiment is not contradicted, the sequence of execution may be changed, a plurality thereof may be performed simultaneously, or the sequence may be changed each time they are performed.

Although the above-noted embodiment has been described for the case in which the treatment apparatus 10 and the medical image processing apparatus 100 are separate apparatuses, the treatment apparatus 10 and the medical image processing apparatus 100 may be integrated into one apparatus. If the treatment apparatus 10 and the medical image processing apparatus 100 are separated apparatuses, the controller 15 may be a function that is built into the medical image processing apparatus 100.

Figure 18:
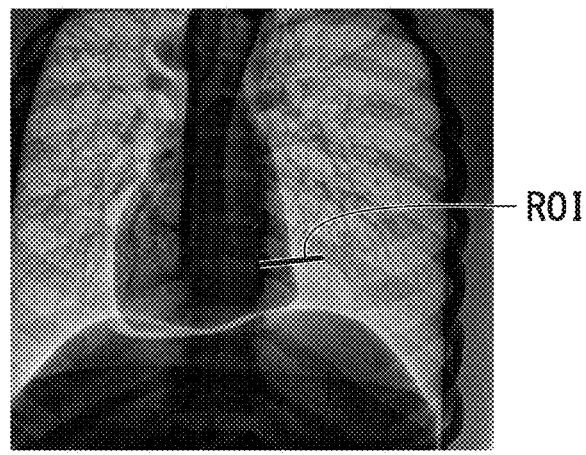
FIG. 18 shows another example of an ROI specified in the DRR.
Figure 19:
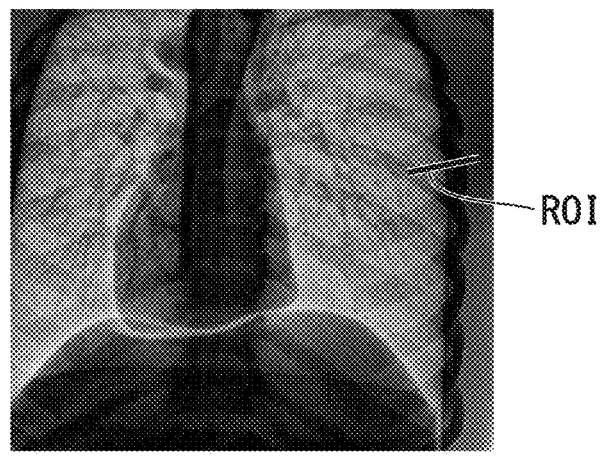
FIG. 19 shows another example of an ROI specified in the DRR.
Figure 20:
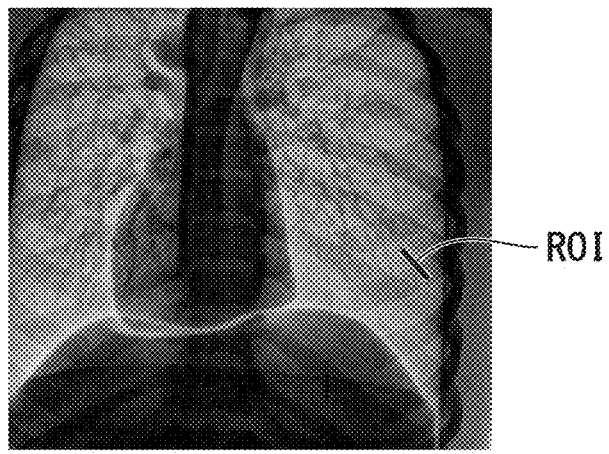
FIG. 20 shows another example of an ROI specified in the DRR.

The ROI is not restricted to that shown in FIG. 7, and can be specified in various forms. FIG. 18 to FIG. 21 shows other examples of the ROI specified in the DRR. In the example of FIG. 18, the heart wall is detected as the landmark. In the example of FIG. 19, the thoracic wall is detected as the landmark. In the example of FIG. 20, a bone (rib bone) is detected as the landmark. In this manner, it is preferable that a part relatively clearly shown in the input be taken as the landmark. As described above, the landmark need not be a single type, and is preferably several types.

Figure 21:
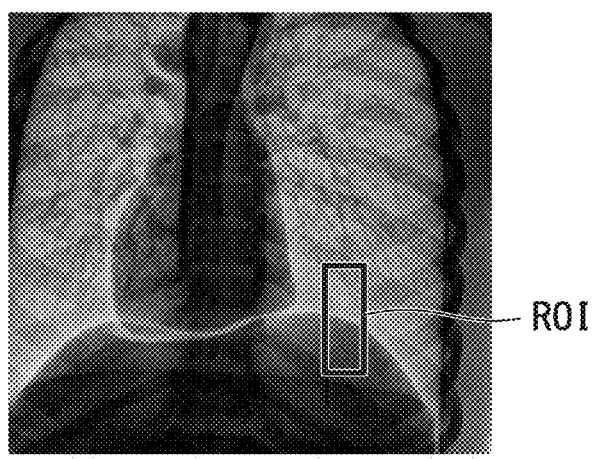
FIG. 21 shows another example of an ROI specified in the DRR.
Figure 22:
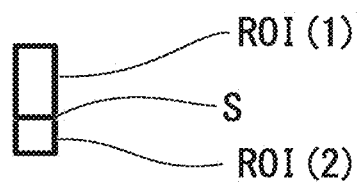
FIG. 22 shows the relationship between a dividing position S and the divided ROI(1) and ROI(2).
Figure 23:
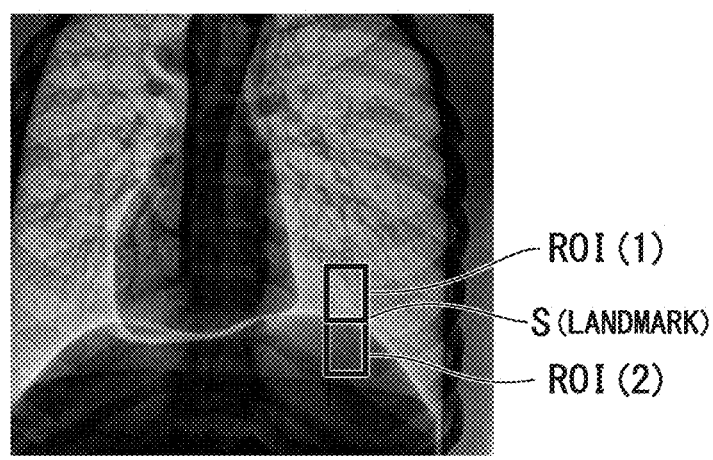
FIG. 23 shows a dividing position S detected as a landmark.

As shown in FIG. 21, the ROI may be specified as a region such as a rectangle, in which case, as shown in FIG. 22, the learning-stage landmark detector 112 or the rehearsal/treatment-stage landmark detector 120, for example, divides the ROI into two, changing the dividing positions by a prescribed width step. As shown in FIG. 23, the dividing position S at which the degree of separation between the divided ROI(1) and ROI(2) is maximum is detected as the landmark. If the region of interest is specified as a region such as a rectangle, the user may be enabled to select whether the ROI is divided left-and-right in the case of horizontally-long rectangular shape or top-and-bottom in the case of vertically-long rectangular shape. In this case, the method of division can be selected by the used by radio buttons. Alternatively, the setting of whether the ROI is divided left-and-right or top-and-bottom may be made automatically. The setting may be made so that the division is done by the method that results in the larger of the differences between the average density values between the partial regions having same sizes of division of the ROI in two left-and-right and division of the ROI in two top-and-bottom.

Although the degree of separation has been taken to be the difference in the average value of the densities between the two partial ROI(1) and ROI(2), another calculation method may be adopted. For example, the degree of separation may be defined so that, in the input image, the part above the border of the thoracic diaphragm is bright and the part thereabove is dark, if the trend was originally the reverse of this. The correlation ratio between the density values of the two partial ROI(1) and ROI(2) may be taken as the degree of separation.

The medical image processing apparatus 100 may detect the landmark automatically from the perspective images TI-1 and TI-2 or the DRR by image processing, without the user making input regarding the ROI. For example, the medical image processing apparatus 100 may extract a corner from the perspective images TI-1 and Ti-2 or DRR and detect the position thereof as the landmark. Alternatively, the medical image processing apparatus 100 may detect the edge by image processing of the perspective images TI-1 and TI-2 or the DRR and may detect a position tangent to the x axis, the y axis or having a prescribed slope as the position of the landmark. Alternatively, the medical image processing apparatus 100 may detect the edge by image processing of the perspective images TI-1 and TI-2 or the DRR and may detect a position that intersects with a prescribed straight line as the position of the landmark. Alternatively, the medical image processing apparatus 100 may, based on the CT values from the CT image of the lung, detect the lung field by detecting the air part and, by capturing the position of the lower part of the lung field in the DRR, may detect the position of the thoracic diaphragm in the DRR as the landmark.

As described above, the treatment beam B includes, for example, an X-ray, a g-ray, an electron beam, a proton beam, a neutron beam, or a heavy particle beam. The image used for the treating planning is not restricted to being a 4D CT image, and may be a movie of three-dimensional volume data. For example, the image may be an MRI (magnetic resonance imaging) image.

If treatment is done by the gated irradiation method, the learning module 116 may learn a separate function regarding only the expiration at which the gated irradiation is done. Specifically, if the y coordinate of the thoracic diaphragm is small, that is, if the thoracic diaphragm is on the head side in the head-to-foot direction, a separate function may be learned. This enables a reduction of the error in the expiration, when gated irradiation is done. Although the learning module 116 makes the function model a second-order polynomial, the function model may be a first-order polynomial, polynomial of an order higher than three, or a trigonometric polynomial. Although the learning module 116 is made to learn a common function, regardless of the respiratory phase, when the object to be treated P is inhaling and when the object to be treated P is exhaling, separate functions may be learned. Whether the object to be treated P is inhaling or exhaling can be distinguished by whether a value representing the position of the landmark of the thoracic diaphragm or the like is increasing or decreasing with the elapse of time. Therefore, different functions may be learned when the value increased and when the value is decreased.

Although in the above-noted embodiment the learning module 116 performed learning by using the y coordinate $y_d$ of the thoracic diaphragm and the x coordinate $x_h$ of the heart wall, learning may be done with fewer or more positions of a landmark than that. For example, learning may be done using the x coordinate of the thoracic diaphragm, the y coordinate of the heart wall, the x coordinate of the thoracic wall, the y coordinate of the thoracic wall, the x coordinate of a bone, and the y coordinate of the bone, and the like. A respiration sensor may be mounted to the object to be treated P and the output value from the sensor may added to the input side of the relationship. That is, the learning module 116 may learn the relationship between the position of the landmark, the sensor output value, and the position of the affected area. However, if a respiration sensor is used, a physician, a technician, or a nurse must perform the task of mounting the respiration sensor to the object to be treated P. Stated conversely, in an embodiment in which a respiration sensor is not mounted, because it is not necessary to perform the task of mounting the respiration sensor to the object to be treated P, it is possible to achieve an improvement in energy efficiency of treatment, compared to the conventional case in which a respiration sensor is used.

Although in the above-noted embodiment the position of the affected area of the object to be treated P is set using information of the contour generated by deformable registration from information of the contour of the affected area specified by the user, the user may be made to directly specify the center position in the perspective images TI-1 and TI-2 of the affected area of the object to be treated P. The user uses a mouse or the cursor keys of a keyboard to specify the center position of the affected area of the object to be treated P on a plurality of perspective images TI of different respiratory phases. In this case, the sequence of processing is that of planning treatment, capturing a movie of the perspective images TI-1 and TI-2, learning the relationship, rehearsal, and treatment. Because this enables learning from an image at a time that is closer to the treatment time than the treatment planning time, it enables a reduction in the error in tracking a lesion during treatment.

Also, in the above-noted embodiment, the relationship information indicting the relationship between the position of the landmark and the position of the affected area may indicate the relationship between the positions of a time sequence of landmarks and the position of the affected area. In this case, the estimator 122, based both on the position of the landmark input in the past before the time of estimation and on the position of the landmark input at the time of estimation, estimates the position of the affected area on the object to be treated P. This increases the input information used in the estimation and improves the estimation accuracy.

Second Embodiment

The second embodiment will now be described.

The method of Non-Patent Reference 1 has been known as a method for tracking the movement of an affected area. In this method, a plurality of sets of a partial image at a prescribed position from a movie of the landmark imaged before treatment and a position of a lesion in the partial image are created beforehand. Matching is then done between the plurality of partial images and the partial regions at the same positions in each frame of the movie of the perspective images during treatment. As a result, the position of the lesion paired with the partial image for which the error is minimum is taken to be the estimated position of the lesion. This tracks the lesion from the movie of the perspective image during treatment.

Figure 24:
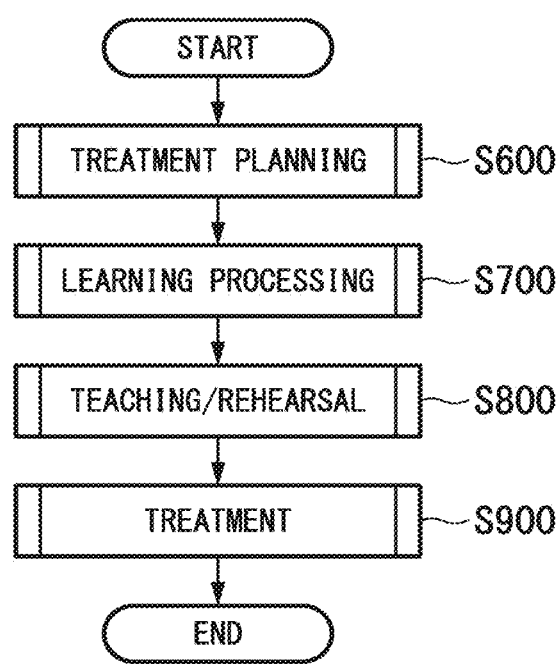
FIG. 24 shows a flowchart indicating the flow of treatment performed using the treatment system 1 according to a second embodiment.

In this method, it is necessary to teach the position of the lesion in the movie of the perspective image imaged before treatment. When this teaching task is done manually, it is troublesome for the user. In the second embodiment, in order to automate the teaching task, various functions described regarding the first embodiment are used. FIG. 24 is an example of a flowchart showing the flow of treatment performed using the treatment system 1 according to the second embodiment. Because the treatment planning (step S600) and the learning processing (step S700) are the same as steps S200 and S300 in FIG. 2, the descriptions thereof will be omitted.

In the teaching/rehearsal processing (step S800), each frame of the movies of the perspective images TI-1 and TI-2 is imaged and the center position of the affected area of the object to be treated P is estimated. Then, on the input/display 110 or the display 17, each frame of the movies of the perspective images TI-1 and TI-2 and the positions of the affected area estimated in each of the frames are display superimposed. The frames of the movies can be freely changed by the user making an operation with a mouse or a keyboard. In the following, the user input will be accepted by the input/display 110 or the input device 16.

While viewing the display screen, the user judges whether or not the position of an object indicating the estimated position of the affected area in each frame is proper and, if it is not proper, the user uses a mouse or the cursor keys of a keyboard to specify the true position of the affected area. The user uses a mouse to specify the position, size, and shape and the like of the partial image of interest.

Each frame of the movies of the perspective images TI-1 and TI-2 are sent to the controller 15. The controller 15 stores in an attached storage (not shown) the sets of the partial images of each frame of the movies of the perspective images TI-1 and TI-2 and the positions of the affected area.

The controller 15, using the sets of stored partial images and lesion positions, tracks the position of the affected area from the movies of the perspective images TI-1 and TI-2 by the method of Non-Patent Reference 1. The status of the tracking is display by either the input/display 110 or the display 17.

In the treatment stage (step S900), the affected area of the object to be treated P is irradiated by the treatment beam B. For this purpose, the movies of the perspective images TI-1 and TI-2 are imaged. The controller 15 acquires each frame of the movies of the perspective images TI-1 and TI-2 and, using sets of the partial images and affected area positions that had been stored in the storage, tracks the position of the affected area, using the method of Non-Patent Reference 1. The controller 15, based on information regarding the treatment plan that is stored in the storage, outputs a control signal to the irradiation port 14 so as to irradiate with the treatment beam B. The irradiation port 14 irradiates with the treatment beam B in accordance with that control signal. This results in the affected area of the object to be treated P being treated by the gated irradiation method or the tracking irradiation method.

The treatment system according to the second embodiment, in addition to tracking the position of the affected area using the method of Non-Patent Reference 1, performs control, based on the center position of the affected area output by the medical image processing apparatus 100 so as to irradiate with the treatment beam B. As a result, because the treatment system according to the second embodiment does not need to image CT images of various respiratory phases separate from the images for treatment plan immediately before treatment, the user can treat the object to be treated P without having to perform that task. It is also possible to lighten the burden of teaching the position of the affected area in the method of Non-Patent Reference 1.

Although the medical image processing apparatus 100 has been used in the second embodiment to teach the position of the affected area using the method described in Non-Patent Reference 1, there is no restriction to using the method of Non-Patent Reference 1, and the medical image processing apparatus 100 may be used in the same manner with another tracking method that is required to teach the position of the affected area.

A medical image processing method described in the above-noted embodiments is a method in which a computer acquires a perspective image of an object to be treated imaged by an imaging apparatus, detects the position of a landmark in the acquired perspective image and, based on relationship information indicating the relationship between the position of the landmark and the position of the location being target, estimates the position of the location being target in the object to be treated from the detected position of the landmark.

A medical image processing program described in the above-noted embodiments is a program that causes a computer to detect the position of a landmark in a perspective image of an object to be treated imaged by an imaging apparatus, and, based on relationship information indicating the relationship between the position of the landmark and the location being target, to estimate the position of the location being target in the object to be treated from the detected position of the landmark.

According to some embodiments, by having acquisitors 104-1 and 104-2 that acquire a perspective image of an object to be treated imaged by imaging apparatuses 13-1 and 13-2, first landmark detectors 120-1 and 120-2 that detect the position of a landmark that appears in the perspective images TI-1 and TI-2 acquired by the acquisitors, and estimators 122-1 and 122-2 that estimate the position of an affected area of an object to be treated P from the position of a landmark detected by the first landmark detectors based on relationship information indicating the relationship between the position of the landmark and the position of the affected area, it is possible to improve the reliability of treatment.

Although a number of embodiments of the present invention are described above, these embodiments are provided as examples, and are not intended to restrict the scope of the invention. These embodiments can be made in other various forms and can be subjected to various omissions, replacements, and modifications, within the scope of the spirit of the invention. Just as these embodiments and their variations are included in the scope and spirit of the invention, they are included in the scope of inventions recited in the claims and the equivalents thereto.

The invention claimed is:

1. A medical apparatus comprising:
    an acquisitor that acquires a perspective image including a treatment target;
    a first landmark detector that detects a position of a landmark included in the image, which is characteristic part with respect to an image surrounding the treatment target, in the perspective image;
    an estimator that, estimates the position of the treatment target based on the position of the landmark detected by the first landmark detector and relationship information indicating a relationship in position between the landmark and the treatment target; and
    a controller that, if the position of the treatment target estimated by the estimator is within a set range, controls an irradiation port to irradiate with a treatment beam,
    wherein
    the relationship information is obtained by acquiring positions of a plurality of landmarks in each of a plurality of images in different respiratory phases having a picture angle that is the same as the perspective image and learning relationship between the positions of the plurality of the landmarks and the positions of the plurality of treatment targets on at least one common respiratory phase,
    the relationship information includes a parameter of a function for deriving the position of the treatment target from the position of the landmark.

2. The apparatus according to claim 1, further comprising a display that displays an image,
    wherein the estimator controls the display to display a symbol that indicates the position of the estimated treatment target wherein the symbol is superimposed on the perspective image.

3. The apparatus according to claim 2, further comprising an input device that accepts a correction operation of a position of the treatment target,
    wherein the display displays the symbol, which has been changed in position in accordance with the correction operation, superimposed on the perspective image.

4. The apparatus according to claim 1,
    wherein the acquisitor acquires a plurality of images in different respiratory phases,
    the estimator estimates the position of the treatment target in different respiratory phases, based on the relationship information in different respiratory phases.

5. The apparatus according to claim 4, further comprising:
    a learning module that acquires positions of a plurality of landmarks in each of a plurality of images in different respiratory phases having a picture angle that is the same as the perspective image, and based on positions of the plurality of the landmarks and positions of the plurality of the treatment targets on at least one common respiratory phase, the learning module learning the relationship information.

6. The apparatus according to claim 5, wherein the plurality of images are generated from a movie of three-dimensional volume data, and further comprising:
    a target position calculator that, develops information specified by the user regarding three-dimensional volume data having at least one respiratory phase of the movie of the three-dimensional volume data into images for other respiratory phases, and the target position calculator deriving the position of a treatment target in the plurality of images.

7. The apparatus according to claim 5, further comprising:
    an input device that accepts an input operation from a user; and
    a second landmark detector that detects, either within a region of interest or in the vicinity of the region of interest specified by a user using the input device, a position of the landmark in the plurality of images,
    wherein the learning module acquires the positions of the plurality of landmarks in the plurality of images of different respiratory phases from the second landmark detector.

8. The apparatus according to claim 1, wherein the landmark includes at least one point on a contour line of one of a thoracic diaphragm, a heart wall, a thoracic wall, and a bone.

9. The apparatus according to claim 1,
    wherein the relationship information indicates relationships in position between the landmarks and the treatment targets at different times in one cycle of the respiratory phases.

10. The apparatus according to claim 1, wherein the position of the landmark and the position of the treatment target are deferent from each other in a respiratory phase.

11. The apparatus according to claim 1, wherein the plurality of images in different respiratory phases having a picture angle that is the same as the perspective image, is a plurality of DRR (digitally reconstructed radiograph)s being generated from 4D CT or 4D MRI.

12. The apparatus according to claim 1, wherein the positions of the plurality of treatment targets are set based on contour input by a physician or a radiologic technologist.

13. A treatment system comprising:
an acquisitor that acquires a perspective image including a treatment target, the perspective image being imaged by an imaging apparatus;
a first landmark detector that detects a position of a landmark that appears in the perspective image acquired by the acquisitor, the landmark being characteristic part with respect to an image surrounding the treatment target;
an estimator that, based on a relationship information indicating a relationship between the position of the landmark and the position of the treatment target, estimates the position of the treatment target from the position of the landmark detected by the first landmark detector;
an irradiation port that irradiates the treatment target with a treatment beam; and
a controller that, if the position of the treatment target estimated by the estimator is within a set range, controls the irradiation port to irradiate with the treatment beam,
wherein
the relationship information is obtained by acquiring positions of a plurality of landmarks in each of a plurality of images in different respiratory phases having a picture angle that is the same as the perspective image and learning relationship between the positions of the plurality of the landmarks and the positions of the plurality of treatment targets on at least one common respiratory phase,
the relationship information includes a parameter of a function for deriving the position of the treatment target from the position of the landmark.

14. The system according to claim 13, wherein the position of the landmark and the position of the treatment target are deferent from each other in a respiratory phase.

15. A method comprising:
acquiring an image including a treatment target imaged by an imaging apparatus,
detecting a position of a landmark in the acquired image,
estimating, based on relationship information indicating a relationship between the position of the landmark and the position of a treatment target, the position of the treatment target from the detected position of the landmark, and
controlling an irradiation port to irradiate with a treatment beam, if the position of the treatment target estimated by the estimating is within a set range,
wherein
the relationship information is obtained by acquiring positions of a plurality of landmarks in each of a plurality of images in different respiratory phases having a picture angle that is the same as a perspective image and learning relationship between the positions of the plurality of the landmarks and positions of the plurality of treatment targets on at least one common respiratory phase,
the relationship information includes a parameter of a function for deriving the position of the treatment target from the position of the landmark.

16. A medical image processing apparatus comprising:
an acquisitor that acquires a perspective image including a treatment target;
a first landmark detector that detects a position of a landmark, which is characteristic part with respect to an image surrounding the treatment target, in the perspective image;
an estimator that estimates a position of a treatment target based on the position of the landmark detected by the first landmark detector and relationship information indicating a relationship in position between the landmark and the treatment target; and
a controller that, if the position of the treatment target estimated by the estimator is within a set range, controls an irradiation port to irradiate with a treatment beam,
wherein
the relationship information is based on a first contour information of the treatment target input into one of a plurality of three-dimensional volume data, which include images of the treatment target imaged at different times from each other, and a second contour information set by registration using the first contour information for the rest of the plurality of three-dimensional volume data.

17. The apparatus according to claim 16, wherein the estimator estimates the position of the treatment target based on two or more landmarks positioned in different directions from the treatment target.

18. The apparatus according to claim 16, wherein the estimator estimates the position of the treatment target based on three or less coordinate components among four coordinate components included in coordinates of two landmarks.

19. The apparatus according to claim 16, wherein the relationship information indicates relationship in position between the landmark and the treatment target in a respiratory phase same as the respiratory phase of the perspective image.

20. The apparatus according to claim 16, wherein the position of the landmark and the position of the treatment target are different from each other in a respiratory phase.

21. A medical image processing apparatus comprising:
an acquisitor that acquires a perspective image including a treatment target;
a first landmark detector that detects a position of a landmark, which is characteristic part with respect to an image surrounding the treatment target, in the perspective image;
an estimator that estimates a position of the treatment target based on the position of the landmark detected by the first landmark detector and relationship information indicating a relationship in position between the landmark and the treatment target;
a controller that, if the position of the treatment target estimated by the estimator is within a set range, controls an irradiation port to irradiate with a treatment beam; and
a storage storing a treatment plan of irradiation of a treatment beam, the treatment plan being generated by acquiring a plurality of images imaged at different times from each other, each of the plurality of images including an image of the treatment target, accepting an input operation specifying a partial region of one image among the plurality of images, and setting to other images among the plurality of images a region associated with the partial region by registration.

22. The apparatus according to claim 21, wherein the position of the landmark and the position of the treatment target are deferent from each other in a respiratory phase.

* * * * *